(12) United States Patent
Tavassolian et al.

(10) Patent No.: US 10,976,428 B2
(45) Date of Patent: Apr. 13, 2021

(54) SYNTHETIC ULTRA-WIDEBAND MILLIMETER-WAVE IMAGING FOR TISSUE DIAGNOSTICS

(71) Applicant: THE TRUSTEES OF THE STEVENS INSTITUTE OF TECHNOLOGY, Hoboken, NJ (US)

(72) Inventors: Negar Tavassolian, Hoboken, NJ (US); Amir Mirbeik-Sabzevari, Weehawken, NJ (US)

(73) Assignee: THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 0 days.

(21) Appl. No.: 16/275,149

(22) Filed: Feb. 13, 2019

(65) Prior Publication Data
US 2019/0179008 A1 Jun. 13, 2019

Related U.S. Application Data

(63) Continuation-in-part of application No. 15/895,991, filed on Feb. 13, 2018.
(Continued)

(51) Int. Cl.
*G01S 13/90* (2006.01)
*A61B 5/05* (2021.01)
(Continued)

(52) U.S. Cl.
CPC .............. *G01S 13/90* (2013.01); *A61B 5/05* (2013.01); *G01S 13/0209* (2013.01);
(Continued)

(58) Field of Classification Search
CPC .................................. G01S 13/89; A61B 5/05
See application file for complete search history.

(56) References Cited

U.S. PATENT DOCUMENTS 4,680,538 A * 7/1987 Dalman ................. G01R 27/04
324/601
5,945,940 A * 8/1999 Cuomo .................... G01S 7/412
342/195

(Continued)

OTHER PUBLICATIONS

Mirbeik-Sabzevari et al., "Ultra-Wideband Millimeter-Wave Dielectric Characteristics of Freshly-Excised Normal and Malignant Human Skin Tissues," IEEE Transactions on Biomedical Engineering, vol. 65, No. 6, Jun. 2018.

(Continued)

*Primary Examiner* — Marcus E Windrich
(74) *Attorney, Agent, or Firm* — Lewis Roca Rothgerber Christie LLP

(57) ABSTRACT

The present disclosure relates to an apparatus and method for synthetically making an ultra-wide imaging bandwidth in millimeter-wave frequencies, resulting in improved image resolutions to values previously unattained. The synthetic approach sums up a number of available sub-bands (channels) to build an unavailable ultra-wideband system. Each channel contains an antenna unit which is optimized for operation within that specific sub-band. The number and position of the channels can be adjusted to cover any frequency range as required for the specific application.

20 Claims, 4 Drawing Sheets
(3 of 4 Drawing Sheet(s) Filed in Color)

Related U.S. Application Data

(60) Provisional application No. 62/458,890, filed on Feb. 14, 2017, provisional application No. 62/630,167, filed on Feb. 13, 2018.

(51) Int. Cl.
*G01S 13/02* (2006.01)
*H01Q 13/08* (2006.01)
*G01S 13/89* (2006.01)
*A61B 5/00* (2006.01)
*G01S 13/34* (2006.01)
*G01S 7/03* (2006.01)

(52) U.S. Cl.
CPC .............. *G01S 13/89* (2013.01); *H01Q 13/08* (2013.01); *A61B 5/444* (2013.01); *G01S 7/03* (2013.01); *G01S 13/347* (2013.01)

(56) References Cited

U.S. PATENT DOCUMENTS

| | | | | |
|---|---|---|---|---|
| 6,373,432 B1* | 4/2002 | Rabinowitz | ............. | G01S 19/04 342/3 |
| 6,466,958 B1* | 10/2002 | Van Wechel | ............ | G01S 19/24 342/357.68 |
| 9,265,438 B2* | 2/2016 | Weinstein | ............ | A61B 5/6823 |
| 9,372,256 B2 | 6/2016 | Mohamadi | | |
| 2002/0140616 A1* | 10/2002 | Kanamaluru | ........ | H01Q 21/064 343/756 |
| 2003/0138060 A1* | 7/2003 | Alcouffe | ............. | H04L 27/2662 375/324 |
| 2004/0264626 A1* | 12/2004 | Besson | ................... | A61B 6/563 378/4 |
| 2005/0270231 A1* | 12/2005 | Small | ...................... | G01S 7/282 342/194 |
| 2009/0289833 A1* | 11/2009 | Johnson | ............... | H01Q 21/061 342/118 |
| 2010/0225520 A1* | 9/2010 | Mohamadi | .......... | G01S 13/0209 342/21 |
| 2013/0307716 A1* | 11/2013 | Mohamadi | ............ | G01S 13/887 342/22 |
| 2016/0124069 A1* | 5/2016 | Sendonaris | ............... | G01S 5/10 342/462 |
| 2016/0131754 A1* | 5/2016 | Cornic | ...................... | G01S 3/74 342/156 |
| 2016/0178730 A1* | 6/2016 | Trotta | ..................... | G01S 7/354 342/175 |
| 2016/0377728 A1* | 12/2016 | Kreienkamp | ........... | G01S 19/23 342/357.62 |

OTHER PUBLICATIONS

Mirbeik-Sabzevari et al., "Characterization and Validation of the Slim-Form Open-Ended Coaxial Probe for the Dielectric Characterization of Biological Tissues at Millimeter-Wave Frequencies," IEEE Microwave and Components Letters, vol. 28, No. 1, Jan. 2018.

Mirbeik-Sabzevari et al., "Synthetic Ultra-High Resolution Millimeter-Wave Imaging for Skin Cancer Detection," IEEE Transactions on Biomedical Engineering, vol. 66, No. 1, Jan. 2019.

Mirbeik-Sabzevari et al., "W-Band Micromachined Antipodal Vivaldi Antenna Using SIW and CPW Structures," IEEE Transactions on Antennas and Propagation, vol. 66, Issue 11, Nov. 2018.

* cited by examiner

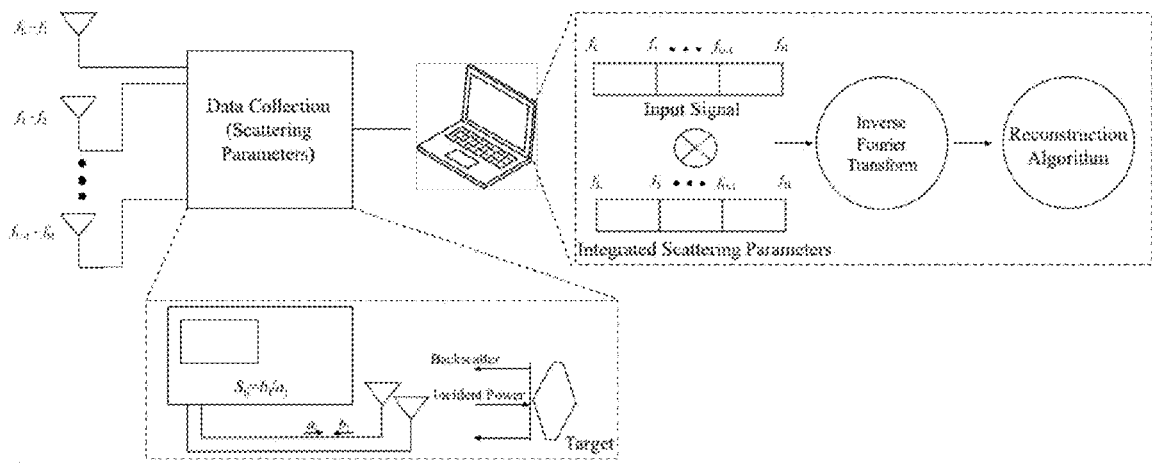
FIG. 5
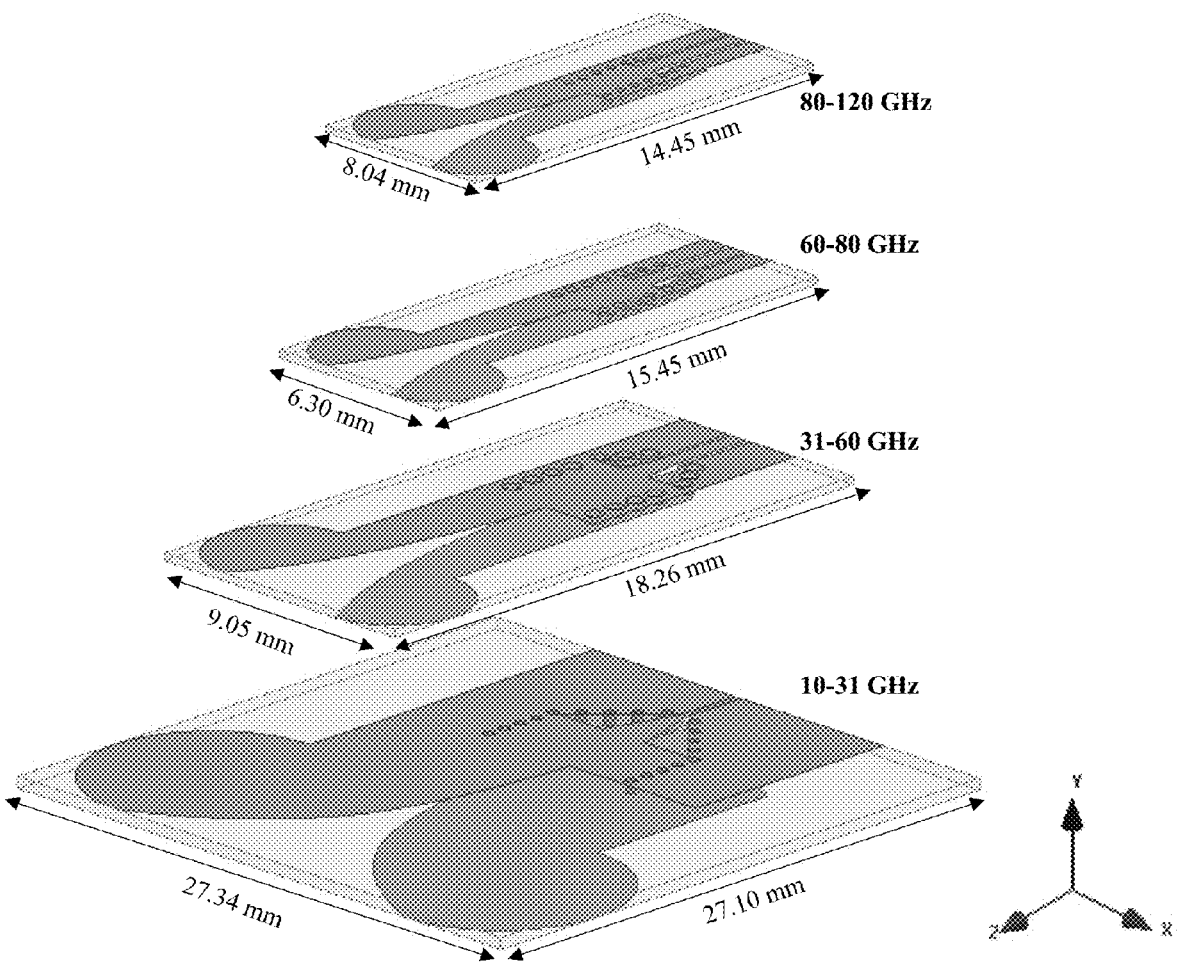
FIG. 6. Schematics of four sub-band SIW-based Vivaldi antennas designed and recently fabricated.

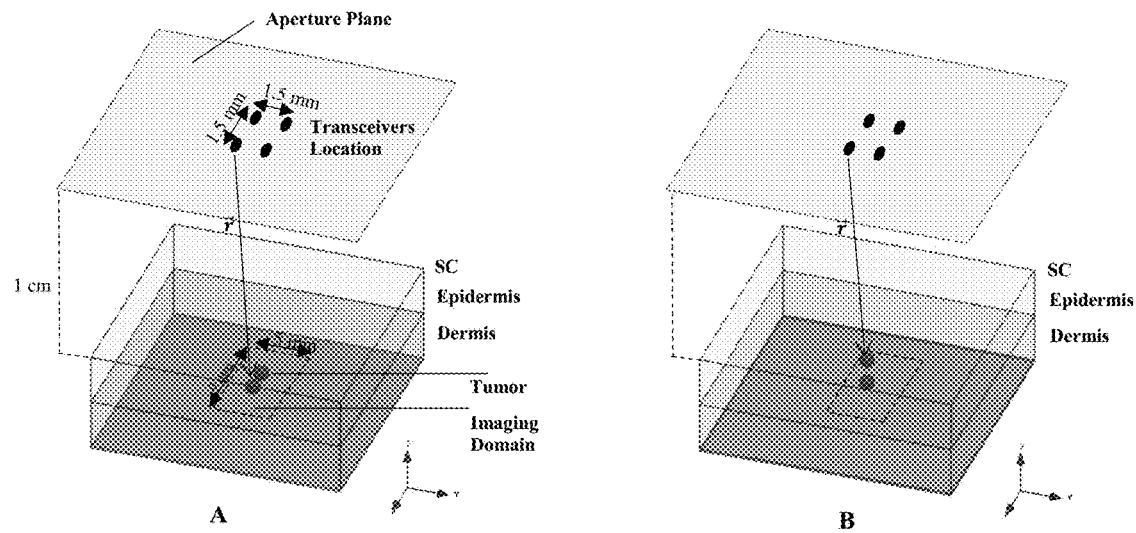
FIG. 7A. Numerical simulation setup for lateral resolution validations.
FIG. 7B. Numerical simulation setup for axial resolution validations.
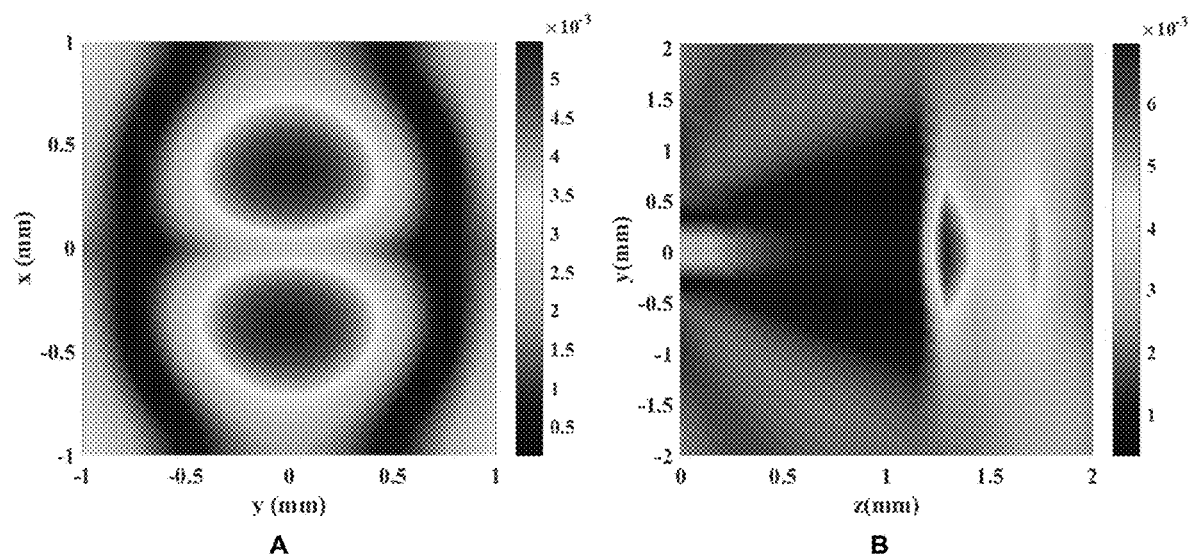
FIG. 8A. Lateral simulated image of a tumor for lateral resolution verification. The tumor is clearly resolved.
FIG. 8B. Sagittal simulated image of a tumor for axial resolution verification. The tumor is clearly resolved.

SYNTHETIC ULTRA-WIDEBAND MILLIMETER-WAVE IMAGING FOR TISSUE DIAGNOSTICS

CROSS-REFERENCE TO RELATED APPLICATION

This application is a continuation-in-part of U.S. patent application Ser. No. 15/895,991 filed Feb. 13, 2018, which claims priority to U.S. Provisional Patent Application Ser. No. 62/458,890 filed Feb. 14, 2017, and claims priority to U.S. Provisional Patent Application Ser. No. 62/630,167 filed Feb. 13, 2018, the entire disclosures of each of the applications listed above being incorporated herein by reference for all purposes.

STATEMENT REGARDING FEDERALLY SPONSORED RESEARCH

This invention was made with government support under Grant No. 1554402 awarded by the National Science Foundation. The government has certain rights in the invention.

FIELD OF THE INVENTION

The present invention relates to millimeter-wave imaging, particularly for biomedical applications.

BACKGROUND OF THE INVENTION

Millimeter-wave imaging is a relatively mature and low-cost imaging technology. However, it has only been applied in military and commercial settings thus far. Despite the various potential advantages of this technology in the biomedical imaging context, such as high image contrasts and suitable penetration depths, it has not been applied in any such applications.

Millimeter-wave imaging is generally performed using wideband techniques (either in frequency or time domain), wherein the image resolution is directly proportional to the bandwidth of the system. There have been no reports of a millimeter-wave imaging system that has the ability to provide the ultra-wideband operation which would be required for accurate tissue imaging. Due to this limitation, no millimeter-wave imaging system has been developed for the purpose of biomedical imaging.

This invention addresses the low image resolutions achieved using current technology by providing significant improvements in the resolution of acquired images. This improvement is achieved by synthesizing an ultra-wide imaging bandwidth that cannot be realized by any conventional design method.

SUMMARY OF THE INVENTION

In view of the foregoing background, an apparatus and method are provided in which several millimeter-wave sub-channels are processed and combined for an ultra-wideband performance, while the sub-channels are successive and disjointed.

In a preferred embodiment, the imaging system is arranged so that the required ultra-wide bandwidth in the millimeter-wave frequencies is divided into a number of sub-channels, wherein each sub-channel separately embraces a sub-band imaging element (antenna). In another preferred embodiment, the sub-band responses are processed and combined to synthesize an integrated signal as if it were collected from an equivalent "virtual" antenna.

As a result of the present invention, an imaging system with an ultra-wide bandwidth in the millimeter-wave frequencies is provided for use with tissue imaging and diagnostic applications. The immediate application of the system is in the early-stage detection of skin cancer. The imaging system can be employed as a reliable and harmless device to help dermatologists with more efficient diagnosis and management of skin cancer. In addition to being used for tissue imaging and biomedical applications, the present invention will allow for millimeter-wave imaging to be used for such applications as dental care (cavity detection) and non-destructive testing (NDT).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention, reference is made to the following detailed description of an embodiment considered in conjunction with the accompanying drawings, in which:

FIG. 5 is a schematic diagram of an embodiment of a method according to the present invention for an integration scheme according to an embodiment of the present invention.

FIG. 6 is a schematic diagram of four sub-band antennas utilized in an application of the imaging scheme according to an embodiment of the present invention;

FIG. 7A is a numerical simulation setup for lateral resolution validations according to an embodiment of the present invention;

FIG. 7B is a numerical simulation setup for axial resolution validations according to an embodiment of the present invention;

FIG. 8A is a lateral simulated image of a tumor for lateral resolution verification, wherein the tumor is clearly resolved by a method of the present invention; and FIG. 8B is a sagittal simulated image of a tumor for axial resolution verification, wherein the tumor is clearly resolved by a method of the present invention.

DETAILED DESCRIPTION OF THE EXEMPLARY EMBODIMENT

The following disclosure is presented to provide an illustration of the general principles of the present invention and is not meant to limit, in any way, the inventive concepts contained herein. Moreover, the particular features described in this section can be used in combination with the other described features in each of the multitude of possible permutations and combinations contained herein.

All terms defined herein should be afforded their broadest possible interpretation, including any implied meanings as dictated by a reading of the specification as well as any words that a person having skill in the art and/or a dictionary, treatise, or similar authority would assign thereto.

Further, it should be noted that, as recited herein, the singular forms "a", "an", "the", and "one" include the plural referents unless otherwise stated. Additionally, the terms "comprises" and "comprising" when used herein specify that certain features are present in that embodiment, however, this phrase should not be interpreted to preclude the presence or additional of additional steps, operations, features, components, and/or groups thereof.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The present invention relates to imaging systems with ultra-wide bandwidths in the millimeter-wave frequencies for tissue imaging and diagnostic applications, and methods for synthesizing same. A main advantage of the systems is their application in the early-stage detection of skin cancer.

To address the need for a method and an apparatus that utilizes millimeter-wave imaging technology for biomedical applications, the concept of "synthetic ultra-wideband imaging" is provided which aims to "synthesize" an ultra-wide imaging bandwidth that cannot be realized using any conventional design method.

Figure 1:
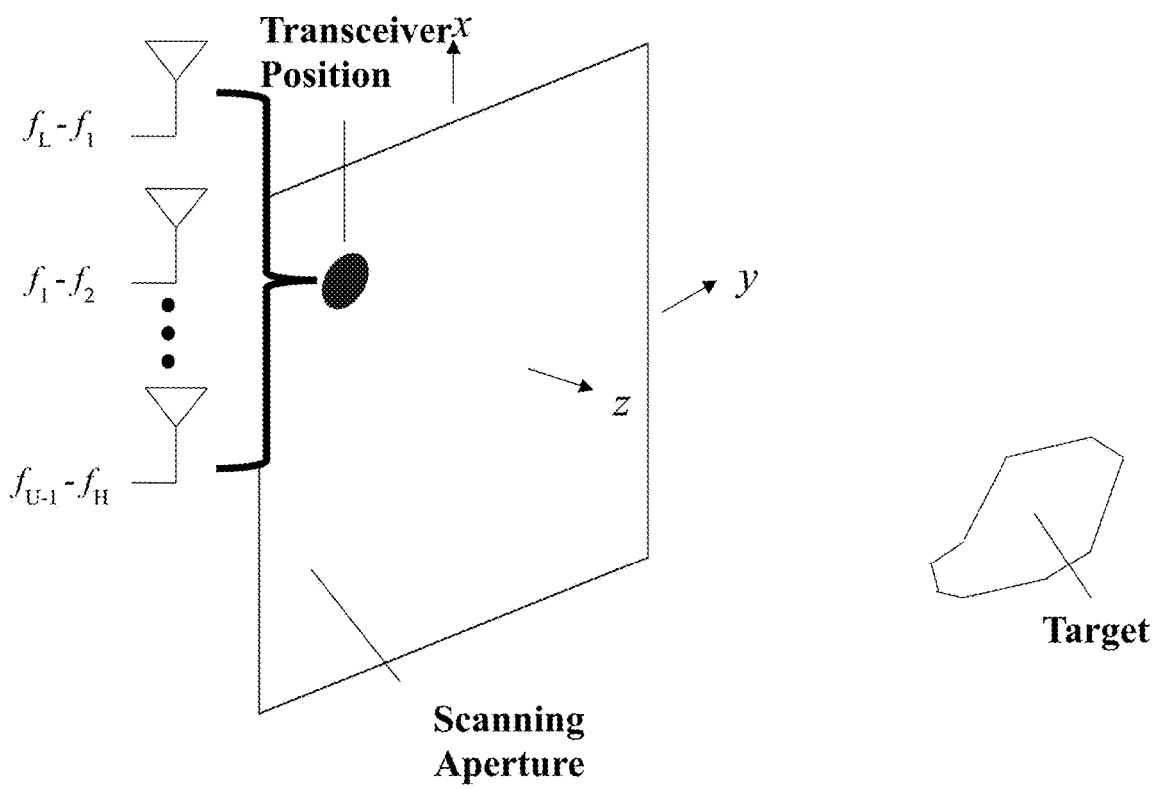
FIG. 1 is a millimeter-wave imaging system in accordance with an embodiment of the present invention.

The present invention is described herein with reference to FIGS. 1-8, which figures illustrate, but do not fully encompass, the invention. The main component of the millimeter-wave imaging system is a planar aperture of antennas which sends millimeter-wave signals to a target of which the image is to be formed, and subsequently picks up (collects) the reflection signals from the target (FIG. 1). Each antenna element can operate both as a transmitter and a receiver. The plane of receiving antennas, which collect the scattered signals from the target may be the same or different than the plane of transmitting antennas. The antennas are normally connected to a millimeter-wave vector network analyzer (VNA) which generates, as well as records, signals over a specific range of millimeter-wave frequencies. After a signal is generated by the VNA, it is radiated as an electromagnetic wave through a transmitting antenna to the space containing the target. The reflected waves from the target are then captured by a receiving antenna connected to the VNA, wherein the incoming backscattered waves are recorded by a millimeter-wave detector. The data collection can be performed either by scanning a transmitting and receiving antenna over a rectilinear planar aperture (i.e. monostatic imaging) or by electronically switching on/off an array comprising multiple antennas (i.e. multi-static imaging). For the latter, the signal is radiated from one antenna to the target (i.e. the antenna acts as a transmitter) and reflections from the target are collected by all of the antennas in the array (i.e. the antennas act as receivers). This process is repeated until all antenna elements have operated as transmitters. In this case, the transmitting/receiving circuitry consists of a switching network, which selects transmitting/receiving antenna pairs successively to be connected to the VNA for generation and recording of the signals.

Figure 2:
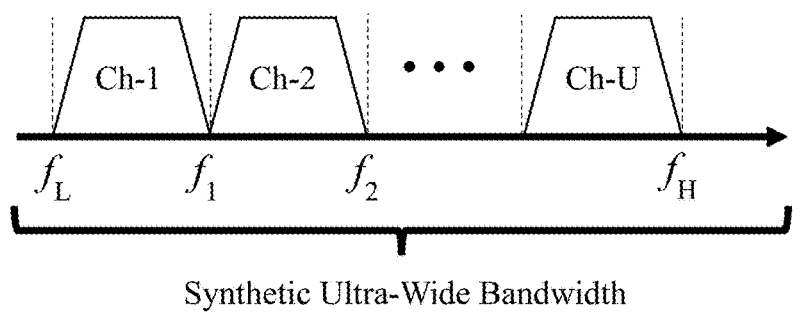
FIG. 2 is a block diagram of the sub-band division scheme employed by the imaging system of FIG. 1 in dividing a frequency bandwidth $(f_L\text{-}f_H)$ into U channels in accordance with another embodiment of the present invention.
Figure 3:
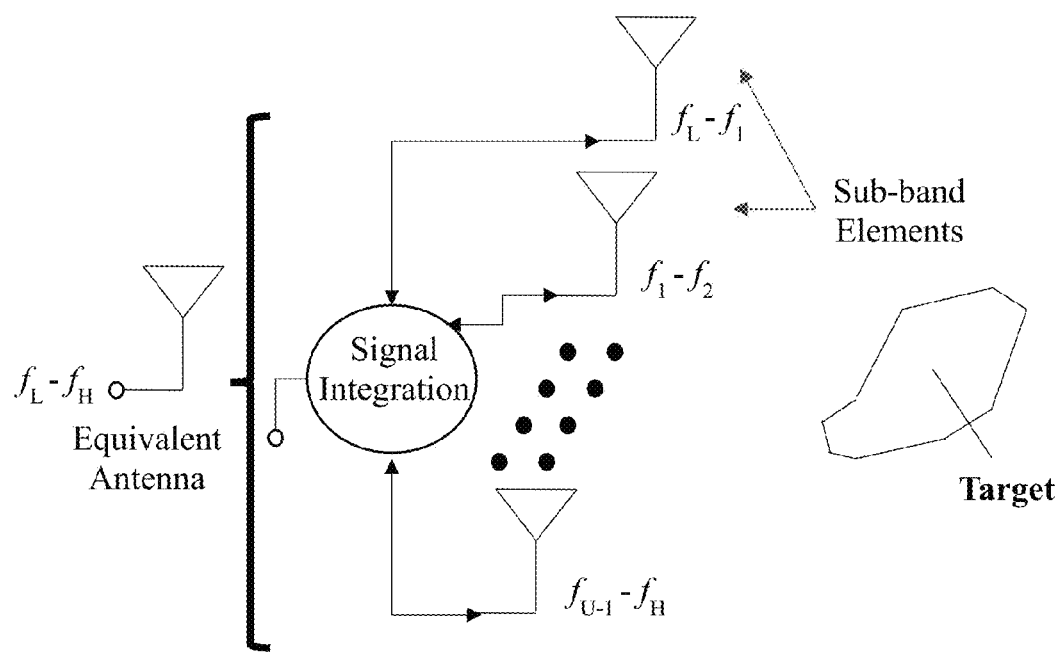
FIG. 3 is a block diagram of the synthetic ultra-wideband scheme employed by the imaging system of FIG. 1 in integrating two or more sub-bands in accordance with an embodiment of the present invention.
Figure 4:
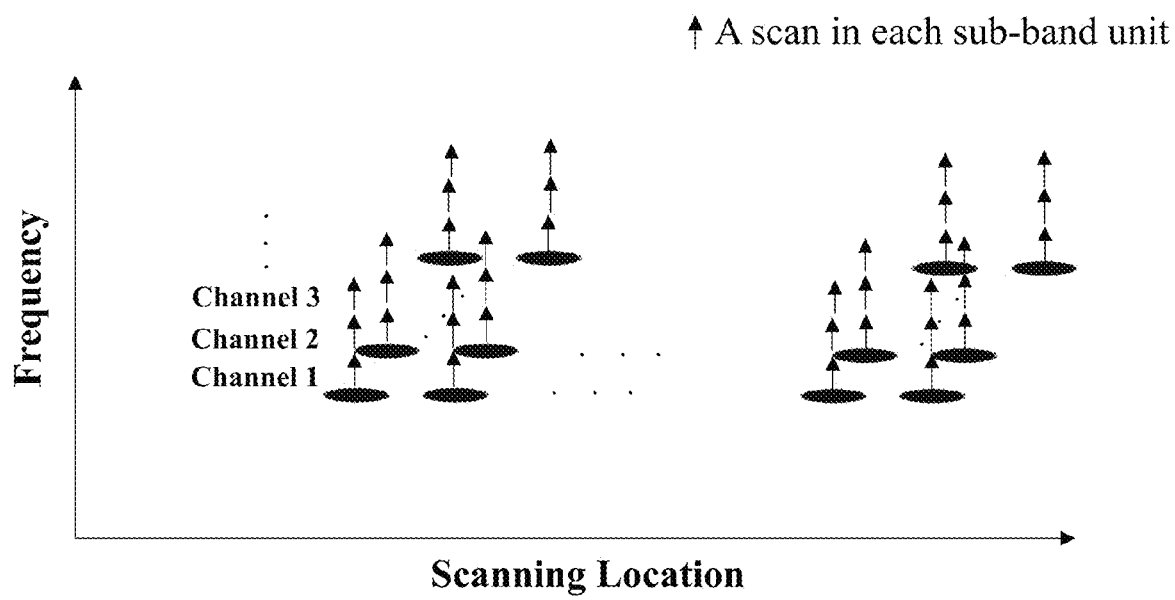
FIG. 4 is a graphical representation of the scan mechanism using the synthetic ultra-wideband approach according to an embodiment of the present invention.

Generally, an embodiment of the present invention encompasses a method by which an ultra-wide imaging frequency range ($f_L$ to $f_H$) is realized by the integration of several disjointed adjacent sub-bands or channels. Each channel corresponds to an antenna unit which operates within that specific sub-band (FIGS. 2, 3). At each scanning location, all the sub-band antennas which operate at a specific sub-band are placed at specified positions in front of the target (these positions are determined according to the Nyquist sampling rate, i.e. the distance between two successive antennas should be less than half of the smallest operating wavelength in which the antennas operate) and sequentially transmit (radiate) the signals originating from a millimeter-wave signal generator (e.g. a VNA) across that specific sub-band to the target (FIG. 4). For each transmitting antenna, the sub-band backscattered signals are recorded for all antenna locations by using a millimeter-wave signal detector (e.g. a VNA) in a similar manner as described earlier. Only one transmission channel will be active at each data collection step as one antenna transmits and one antenna receives the signal. After all antenna pairs have been selected as transceiver/receiver elements, the above process is repeated for all imaging sub-bands.

Another embodiment of the present invention encompasses a method by which the sub-band backscattered responses for each receiver location are combined to synthesize an integrated signal as if it were collected from a virtual antenna operating over the entire bandwidth. This is performed by sequentially arranging the sub-band signals over the frequency domain to cover the whole ultra-wideband range of $f_L$ to $f_H$. For each transmit antenna location, the sub-band scattering parameters are recorded for all antenna pairs ($S_{ij}$-parameters). Only one transmission channel will be active at each data collection step as one antenna element transmits and one receives the signal. The collected sub-band scattering parameters are imported into a computer where a signal integration scheme is used to combine the sub-channels and generate an integrated signal as if it were collected from a virtual equivalent ultra-wideband antenna operating over the entire frequency band (FIG. 5). The integrated signal is used as a transfer function to calculate the pulse response from the incident pulse in the frequency domain. Pulse responses are subsequently converted to time domain by applying an Inverse Fourier Transform (IFT) operation. A suitable reconstruction algorithm (for example the standard delay-and-sum (DAS) or delay-multiply-and-sum (DMAS) algorithms) will be applied to the pulse responses in the time domain to form a 3D image of the target. By using this concept, the challenges of realizing high-performance ultra-wideband antennas in the millimeter-wave regime are alleviated as each individual antenna is optimized within a limited sub-band. This results in excellent image qualities as well as ultra-high image resolutions. The approach is versatile, as the number and position of the channels can be adjusted to cover any frequency range as required for the specific application. The technique can be applied to mono-static as well as multi-static imaging setups.

The feasibility of using of the synthetic ultra-wideband imaging approach for biomedical applications has been investigated using 3-D, full-wave, electromagnetic simulations on dispersive skin models. Specifically, early-stage skin tumors were detected using numerical skin phantoms and tumor models. A system with a synthetic ultra-wide bandwidth of 110 GHz was considered to provide the ultra-high resolutions (~200 μm) required for visualizing and detecting skin tumors. Four millimeter-wave substrate integrated waveguide (SIW)-based antipodal Vivaldi antennas were designed to cover the frequency sub-bands of 10-31 GHz, 31-60 GHz, 60-80 GHz, and 80-120 GHz in order to collectively achieve 110 GHz of bandwidth (FIG. 6). Two spherical tumor models with diameters of 400 μm and a distance of 200 urn (the claimed system resolution) between their closest edges were considered in two separate imaging setups corresponding to lateral (FIG. 7A) and axial resolution (FIG. 7B) verifications respectively. The confocal delay-multiply-and-sum (DMAS) image formation algorithm was applied to the data. The tumors were successfully resolved both axially (FIG. 8A) and laterally (FIG. 8B).

Additional details are presented in the publication by Amir Mirbeik-Sabzevari et al., titled "Ultra-Wideband Millimeter-Wave Dielectric Characteristics of Freshly Excised Normal and Malignant Human Skin Tissues," *IEEE Transactions on Biomedical Engineering*, Vol. 65, No. 6, June 2018, pp. 1320-1329, <URL: https://ieeexplore.ieee.org/document/8026147> <DOI: 10.1109/TBME.2017.2749371>, in the publication by Amir Mirbeik-Sabzevari et al., titled "Synthetic Ultra-High-Resolution Millimeter-Wave Imaging for Skin Cancer Detection," *IEEE Transactions on Biomedical Engineering*, Vol. 66, No. 1, January 2019, pp. 61-71, <URL: https://ieeexplore.ieee.org/abstract/document/8360774> <DOI: 10.1109/TBME.2018.2837102>, in the publication by Amir Mirbeik-Sabzevari et al., titled "W-Band Micromachined Antipodal Vivaldi Antenna Using SIW and CPW Structures," *IEEE Transactions on Antennas and Propagation*, Vol. 66, No. 11, November 2018, pp. 6352-6357, <URL: https://ieeexplore.ieee.org/document/8425012> <DOI: 10.1109/TAP.2018.2863098>, and in the publication by Amir Mirbeik-Sabzevari et al., titled "Characterization and Validation of the Slim-Form Open-Ended Coaxial Probe for the Dielectric Characterization of Biological Tissues at Millimeter-Wave Frequencies," *IEEE Microwave and Wireless Components Letters*, Vol. 28, No. 1, January 2018, pp. 85-87, <URL: https://ieeexplore.ieee.org/document/8123612> <DOI: 10.1109/LMWC.2017.2772187>. The entire disclosures of each of the foregoing publications are incorporated herein by reference and made part of the present disclosure.

It will be understood that the embodiments described herein are merely exemplary and that a person skilled in the art may make many variations and modifications without departing from the spirit and scope of the invention. All such variations and modifications are intended to be included within the scope of the invention, as defined by the appended claims.

We claim:

1. A method comprising the steps of:
transmitting, from each of a plurality of sub-band imaging elements to a target, output signals operating in a corresponding one of a plurality of predetermined sub-bands of a range of millimeter-wave frequencies;
wherein each sub-band imaging element of the plurality of sub-band imaging elements is configured to operate only in its corresponding sub-band which is different from the sub-band of each remaining one of the plurality of sub-band imaging elements;
receiving, at one or more of the plurality of sub-band imaging elements, return signals reflected from the target in response to the performance of the transmitting step for each of the plurality of sub-band imaging elements;
wherein the transmitting and receiving steps are performed sequentially as a cycle for each sub-band imaging element of the plurality of sub-band imaging elements at each of a plurality of scanning locations;
wherein each sub-band imaging element of the plurality of sub-band imaging elements is sequentially positioned at a distinct position in each of the plurality of scanning locations for the performance of the transmitting and receiving steps;
combining, at a processor, the return signals received from the performance of the transmitting and receiving steps to form an integrated signal covering the range of millimeter-wave frequencies; and
using the integrated signal to generate an image of the target.

2. The method of claim 1, wherein the step of using the integrated signal to generate an image of the target includes calculating pulse responses from incident pulses in frequency domain by using the integrated signal.

3. The method of claim 2, wherein the step of using the integrated signal to generate an image of the target includes converting the pulse responses to time domain by using an Inverse Fourier Transform operation.

4. The method of claim 3, wherein the step of using the integrated signal to generate an image of the target includes applying a reconstruction algorithm to the pulse responses to generate the image of the target.

5. The method of claim 1, wherein each successive pair of the plurality of scanning locations are spaced from each other by a distance which is less than half of the smallest operating wavelength in which the sub-band imaging elements of the plurality of sub-band imaging elements operate.

6. The method of claim 5, wherein the distinct positions of the plurality of sub-band imaging elements relative to the target are adjustable.

7. The method of claim 1, wherein each of the plurality of sub-band imaging elements includes an antenna.

8. The method of claim 7, wherein each of the antennas has a size; and wherein the size of each of the antennas is different from the sizes of the other antennas.

9. A device for imaging tissue, comprising:
an imaging element configured to transmit and receive signals operating in a range of millimeter-wave frequencies,
wherein the range of millimeter-wave frequencies are divided into a plurality of predetermined sub-bands,
wherein the imaging element includes a plurality of sub-band imaging elements configured to transmit signals to a target and to receive signals reflected from the target,
wherein each of said plurality of predetermined sub-bands is assigned to one of said plurality of sub-band imaging elements such that each of said plurality of sub-band imaging elements is configured to transmit to the target signals operating in a corresponding one of said plurality of predetermined sub-bands,
wherein each of the plurality of sub-band imaging elements is configured to operate only in its corresponding sub-band which is different from the sub-band assigned to each remaining one of the plurality of sub-band imaging elements;
wherein each sub-band imaging element of the plurality of sub-band imaging elements is configured to be sequentially positioned at a distinct scanning position in each of a plurality of scanning locations, wherein the plurality of sub-band imaging elements is configured so as to transmit, sequentially from each of said plurality of sub-band imaging elements in each of said scanning locations, output signals operating in a corresponding one of the plurality of predetermined sub-bands, and to receive, at one or more of the plurality of sub-band imaging elements, return signals reflected from the target; and a processor connected to the sub-band imaging elements, the processor configured to receive and combine the return signals reflected from the target over each of the plurality of predetermined sub-bands so as to form an integrated signal covering the preset range of millimeter-wave frequencies, whereby the integrated signal is used to generate an image of the target.

10. The device of claim 9, wherein said processor is configured to calculate pulse responses from incident pulses in frequency domain by using the integrated signal.

11. The device of claim 10, wherein said processor is configured to convert the pulse responses to time domain by using an Inverse Fourier Transform operation.

12. The device of claim 11, wherein said processor is configured to apply a reconstruction algorithm to the pulse responses to generate the image of the target.

13. The device of claim 9, further comprising a signal generator connected to said plurality of sub-band imaging elements for generating the output signals, said signal generator including a millimeter-wave vector network analyzer.

14. The device of claim 12, wherein at least one of said plurality of sub-band imaging elements is configured to receive a corresponding one of the return signals reflected from the target in a corresponding one of said plurality of predetermined sub-bands.

15. The device of 14, wherein each successive pair of said plurality of scanning locations are spaced from each other by a distance which is less than half of the smallest operating wavelength in which said sub-band imaging elements of said plurality of sub-band imaging elements operate.

16. The device of claim 15, wherein the distinct positions of said plurality of sub-band imaging elements relative to the target are adjustable.

17. The device of claim 9, wherein each of said plurality of sub-band imaging elements is an antenna.

18. The device of claim 17, wherein each of said antennas has a size; and wherein the size of each of said antennas is different from the sizes of the other antennas.

19. The method of claim 1, wherein the transmitting step includes sequentially positioning each sub-band imaging element of the plurality of sub-band imaging elements at its corresponding distinct position in each of the plurality of scanning locations.

20. The apparatus of claim 9, wherein each of the sub-band imaging elements of the imaging element is configured to be placed sequentially at its corresponding distinct position in each of the plurality of scanning locations.

* * * * *